United States Patent [19]

Hubele et al.

[11] 4,428,964
[45] Jan. 31, 1984

[54] SULFINYL- AND SULFONYLACETANILIDES AND THEIR USE AS MICROBICIDES

[75] Inventors: Adolf Hubele, Magden; Peter Riebli, Basel, both of Switzerland; Wolfgang Eckhardt, Lörrach, Fed. Rep. of Germany; Walter Kunz, Manchester, England

[73] Assignee: Ciba-Geigy Corporation, Ardsley, N.Y.

[21] Appl. No.: 182,197

[22] Filed: Aug. 28, 1980

[30] Foreign Application Priority Data

Aug. 29, 1979 [CH] Switzerland .................. 7831/79

[51] Int. Cl.³ .................. A01N 41/10; C07C 147/13; C07C 147/14
[52] U.S. Cl. .................. 424/309; 560/12
[58] Field of Search .................. 560/12; 424/309

[56] References Cited

U.S. PATENT DOCUMENTS 3,598,859  8/1971  Yates ............................ 560/12
3,780,095  12/1973  Klemm ........................ 560/12
4,151,299  4/1979  Hubele ........................ 560/43

OTHER PUBLICATIONS

Allinger, "Organic Chemistry," pp. 685–686 (1971).

*Primary Examiner*—Michael L. Shippen
*Attorney, Agent, or Firm*—Frederick H. Rabin

[57] ABSTRACT

There are described novel compounds of the formula I defined herein:

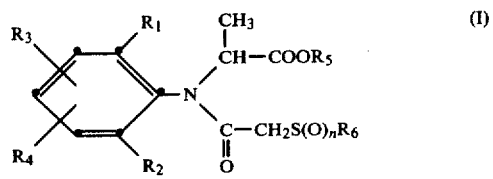

which have valuable microbicidal properties. The novel compounds can be used for combating microorganisms harmful to plants, particularly for combating phytopathogenic fungi. The compounds of the formula I thus have a very favorable curative and preventive action for practical requirements for the protection of cultivated plants, without the plants being impaired as a result of undesirable secondary effects. The compounds can be used in practice on their own or in the form of pesticidal compositions.

17 Claims, No Drawings

SULFINYL- AND SULFONYLACETANILIDES AND THEIR USE AS MICROBICIDES

The present invention relates to a compound of the formula I

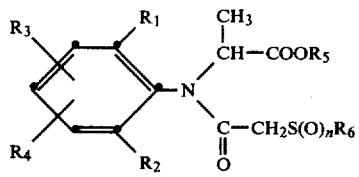

wherein $R_1$ is $C_1$-$C_3$-alkyl, $C_1$-$C_3$-alkoxy or halogen; $R_2$ is $C_1$-$C_3$-alkyl, $C_1$-$C_3$-alkoxy or halogen; $R_3$ is hydrogen, $C_1$-$C_3$-alkyl or halogen; $R_4$ is hydrogen or methyl, $R_5$ is $C_1$-$C_3$-alkyl, $R_6$ is $C_1$-$C_4$-alkyl, and n is 1 or 2.

By alkyl or alkyl moiety of another substituent are meant, depending on the given number of carbon atoms, for example the following groups: methyl, ethyl, propyl and butyl, as well as isomers thereof, for example isopropyl, iso-butyl, sec-butyl, tert-butyl, and so forth. Halogen is fluorine, chlorine, bromine or iodine.

Compounds of the formula I have microbicidal activity.

The compounds of the formula I can be produced by a whole series of methods, for example by the methods given in the following. In the formulae II to XIII, the symbols $R_1$ to $R_6$ and n have the meanings defined under the formula I, "Hal" denotes halogen, preferably chlorine or bromine, and M is hydrogen or a metal cation, preferably an alkali metal cation or alkaline-earth metal cation.

The individual procedures can be as follows:

A. A compound of the formula II is reacted with a thio compound III to give an intermediate product IV, and this is oxidised to obtain the final product I:

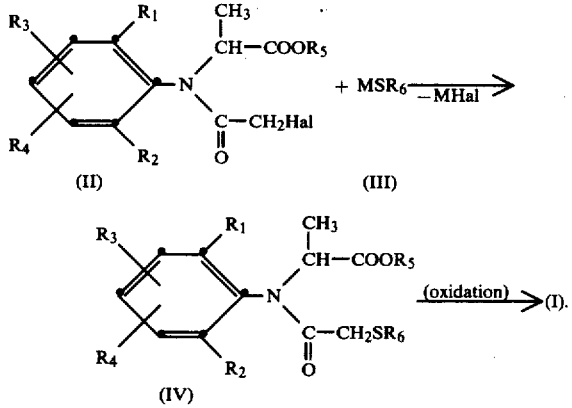

B. A compound of the formula II is reacted directly with a thio compound V to obtain the final product I:

$$(II) + MS(O)_nR_6 \xrightarrow[-MHal]{} (I)$$

(V)

wherein n is 1 or 2.

In the cases where in the processes A and B the substituent M is hydrogen, the use of a salt-forming agent is advantageous, such as an oxide, hydroxide, hydride, and so forth, of alkali metals or alkaline-earth metals.

C. A substituted anilide VI is reacted with an acid halide VII to obtain the final product I:

(VI) + HalC(=O)—CH₂S(O)ₙR₆ (VII) $\xrightarrow{-HHal}$ (I).

D. A substituted anilide VI is reacted with an acid halide VIII to give an intermediate product IV, and this is oxidised, as in process A, to obtain the final product I:

(VI) + HalC(=O)—CH₂SR₆ (VIII) ⟶ (IV) $\xrightarrow{\text{(oxidation)}}$ (I).

E. A substituted aniline IX is reacted with an acid halide X to give an anilide XI, and this is converted with a compound of the formula XII to obtain the final product XIII:

(IX) + HalCCH₂S(O)ₘR₆ (X) $\xrightarrow{-HHal}$ (XI)

(XI) + Hal—CH(CH₃)—COOR₅ (XII) $\xrightarrow{-HHal}$ (XIII)

wherein m can be nought, 1 or 2. In the case where m is nought, an oxidation is necessary, whereby either the product XI or XIII is oxidised. Where m is 1 or m is 2, XIII and I are identical.

F. A substituted aniline IX is reacted with an acid halide XIV to give an anilide XV; this is then converted with a compound of the formula XVI into the intermediate product XI, and this is subsequently converted with an alkyl halide XII to the final product XIII:

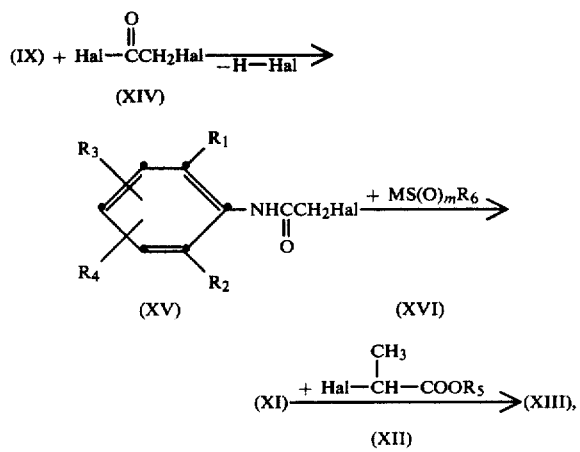

wherein m can be nought, 1 or 2. In the case where m is nought, an oxidation is necessary, whereby either the intermediate product XI or the product XIII (as in process E) is oxidised. Where m is 1 or m is 2, XIII and I are identical.

In the production processes E and F, the compound of the formula XI can advantageously be converted with butyl lithium or sodium hydride firstly into the corresponding alkali salt, or the two processes are performed in the presence of an acid-binding agent.

In the processes A, D, E and F, there can be used for the oxidation of the thioether or sulfoxide group in the compounds of the formulae IV and XIII for example per acids, such as $H_2O_2$, perbenzoic acid, meta-chloroperbenzoic acid, $HJO_4$ or potassium permanganate, and so forth.

In some cases, the use of acid-binding agents or condensation agents is advantageous. Suitable as such are for example: inorganic bases, such as oxides, hydroxides, hydrogen carbonates, carbonates or hydrides of alkali metals and alkaline-earth metals, as well as sodium acetate.

Formed hydrogen halide can however also be expelled from the reaction mixture by the passing through of an inert gas, for example $N_2$.

Solvents which are inert to the reactants can be used in all the processes described. Examples of suitable solvents are: aromatic hydrocarbons, such as benzene, toluene and xylenes; aliphatic hydrocarbons, such as petroleum ether, ligroin and cyclohexane; halogenated hydrocarbons, such as dichloromethane, chloroform, carbon tetrachloride, 1,2-dichloroethane, tetrachloroethylene and chlorobenzene; ethers and ethereal compounds, such as dialkyl ether (diethyl ether, tert-butyl-methyl ether or diisopropyl ether), dimethoxyethane, dioxane, tetrahydrofuran or anisole; nitriles, such as acetonitrile or propionitrile; ketones, such as acetone or methyl ethyl ketone; esters, such as ethyl acetate or butyl acetate; or dimethyl sulfoxide. Also mixtures of solvents of this type with one another can be used.

The various processes likewise form part of the present invention. The starting materials and intermediates of the formulae II, IV and XIII also exhibit a microbicidal action.

All starting materials are known per se and are produced by known methods:

cp. J. Org. Chem. 30, 4104 (1965),
Tetrahedron 1967, 487, and
Tetrahydron 1967, 493.

In the following specifications, acylated anilides are described as being herbicides; there are no references to a fungicidal action, since none of the compounds mentioned therein exhibit any useful fungicidal activity:

U.S. Pat No. 3,966,811
U.S. Pat. No. 3,946,044
U.S. Pat. No. 4,113,464
U.S. Pat. No. 3,946,045
U.S. Pat. No. 3,946,043.

The intermediates of the formulae IV and XIII (m=nought) are known as fungicides from the German Offenlegungsschrift No. 2,515,091. The compounds of the present invention, of the formula I described herein, exhibit however a considerably better fungicidal action compared with that of the substances mentioned in German Offenlegungsschrift No. 2,515,091.

The compounds of the formula I contain, in a position adjacent to the nitrogen atom, an asymmetrical carbon atom in the ester side-chain, and can be split in the customary manner into their optical antipodes. The two enantiomers have different microbicidal properties. The racemate-separation can be performed for example by fractional crystallisation of the salts of VI with an optically active acid (such as L-lactic acid), and further reaction of the optically pure compounds of VI to I.

Depending on substitution, further asymmetrical carbon atoms can be present in the molecule.

Independently of the stated optical isomerism, there is observed an atropisomerism around the >N-phenyl axis when the phenyl nucleus is substituted unsymmetrically with respect to this axis.

If no specific synthesis is carried out for the isolation of pure isomers, a product of the formula I is usually obtained as a mixture of these possible isomers.

Microbicides having the following types of substituents or combinations of these among each other are preferred.

for $R_1$:
(a) $C_1$-$C_2$-alkyl
(b) methyl
(c) methyl;

for $R_2$:
(a) $C_1$-$C_2$-alkyl, $C_1$-$C_2$-alkoxy or halogen
(b) methyl, methoxy or chlorine
(c) methyl;

for $R_3$:
(a) hydrogen, $C_1$-$C_2$-alkyl or halogen
(b) hydrogen, methyl or chlorine
(c) hydrogen, 3-methyl or 3-chlorine;

for $R_4$:
(a) hydrogen or methyl
(b) hydrogen or 5-methyl;

for $R_5$:
(a) $C_1$-$C_3$-alkyl
(b) $C_1$-$C_2$-alkyl
(c) methyl;

for $R_6$:
(a) $C_1$-$C_3$-alkyl;

for n:
(a) 1 or 2
(b) 2.

There are hence given for example the following preferred groups of compounds of the formula I:

A.
$R_1 = C_1$-$C_2$-alkyl $R_2 = C_1-C_2$-alkyl, $C_1-C_2$-alkoxy or halogen
$R_3 =$ hydrogen, $C_1-C_2$-alkyl or halogen
$R_4 =$ hydrogen or methyl
$R_5 = C_1-C_3$-alkyl
$R_6 = C_1-C_3$-alkyl
$n = 1$ or 2.

B.
$R_1 =$ methyl
$R_2 =$ methyl, methoxy or chlorine
$R_3 =$ hydrogen, methyl or chlorine
$R_4 =$ hydrogen or methyl
$R_5 =$ methyl
$R_6 = C_1-C_3$-alkyl
$n = 2$.

C.
$R_1 =$ methyl
$R_2 =$ methyl
$R_3 =$ hydrogen, 3-methyl or 3-chloro
$R_4 =$ hydrogen 5-methyl
$R_5 = C_1-C_2$-alkyl
$R_6 = C_1-C_3$-alkyl
$n = 1$ or 2.

The following individual compounds are particularly preferred by virtue of their very good microbicidal activity:

N-(1'-methoxycarbonyl-ethyl)-N-methylsulfonylacetyl-2,6-dimethylaniline,

N-(1'-methoxycarbonyl-ethyl)-N-ethylsulfonylacetyl-2,6-dimethylaniline, and

N-(1'-methoxycarbonyl-ethyl)-N-methylsulfonylacetyl-2,3,6-trimethylaniline.

The following Examples serve to further illustrate the invention without limiting the scope thereof. The temperature values are given in degrees Centigrade. Unless otherwise stated, the racemic mixture is meant in all cases where reference is made to an active substance of the formula I.

EXAMPLE 1

(a) Production of the intermediate product:

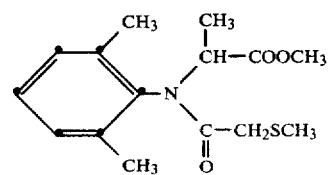
(XIV)

N-(1'-methoxycarbonyl-ethyl)-N-methylthioacetyl-2,6-dimethylaniline.

57.6 g of methyl mercaptan, dissolved in 50 ml of methanol, are added dropwise at room temperature to 650 g of a 10% sodium methylate solution. After the slightly exothermic reaction has subsided, 283.5 g of N-(1'-methoxycarbonylethyl)-N-chloroacetyl)-2,6-dimethylaniline are added portionwise. After 12 hours' stirring, the suspension is filtered, and the filtrate is evaporated to dryness. The oily residue is taken up in diethyl ether, the insoluble part is filtered off, and the filtrate is concentrated in vacuo. After the addition of petroleum ether, there are obtained beige-coloured crystals having a melting point of 65°-67°.

(b) Production of the final product:

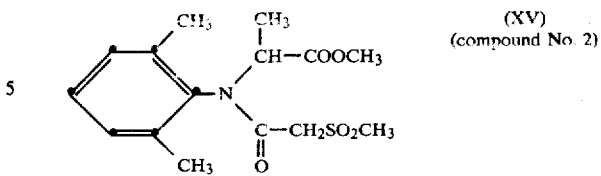
(XV)
(compound No. 2)

N-(1'-methoxycarbonyl-ethyl)-N-methylsulfonylacetyl-2,6-dimethylaniline.

15.5 ml of 30% hydrogen peroxide are added dropwise at 0°, within 30 minutes, to 17 g of N-(1'-methoxycarbonylethyl)-N-methylthioacetyl-2,6-dimethylaniline, produced according to (a), in 250 ml of glacial acetic acid and 250 ml of acetic anhydride. The solution is stirred for 20 minutes at room temperature, and then concentrated in vacuo. The oily residue is taken up in chloroform, washed three times with 250 ml of water each time, dried over sodium sulfate, filtered, and the filtrate is evaporated to dryness. The crystals remaining behind have a melting point of 127°-129°.

The following compounds of the formula I can be produced in the manner described above or by one of the methods described herein.

TABLE I

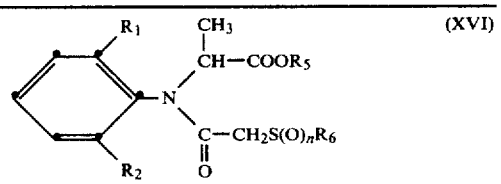
(XVI)

| Comp. No. | $R_1$ | $R_2$ | $R_5$ | $R_6$ | n | Physical constants |
|---|---|---|---|---|---|---|
| 1 | $CH_3$ | $CH_3$ | $CH_3$ | $CH_3$ | 1 | oil |
| 2 | $CH_3$ | $CH_3$ | $CH_3$ | $CH_3$ | 2 | m.p. 127–129° |
| 3 | $CH_3$ | $C_2H_5$ | $CH_3$ | $CH_3$ | 1 | resin |
| 4 | $CH_3$ | $C_2H_5$ | $CH_3$ | $CH_3$ | 2 | m.p. 127–130° |
| 5 | $CH_3$ | $CH_3$ | $C_2H_5$ | $CH_3$ | 1 | resin |
| 6 | $CH_3$ | $CH_3$ | $C_2H_5$ | $CH_3$ | 2 | m.p. 128–130° |
| 7 | $CH_3$ | $CH_3$ | $CH_3$ | $C_2H_5$ | 1 | |
| 8 | $CH_3$ | $CH_3$ | $CH_3$ | $C_2H_5$ | 2 | m.p. 133–134° |
| 9 | $CH_3$ | $C_2H_5$ | $C_2H_5$ | $CH_3$ | 1 | |
| 10 | $CH_3$ | $C_2H_5$ | $C_2H_5$ | $CH_3$ | 2 | m.p. 124–126° |
| 11 | $CH_3$ | $C_2H_5$ | $C_2H_5$ | $C_2H_5$ | 1 | oil |
| 12 | $CH_3$ | $C_2H_5$ | $C_2H_5$ | $C_2H_5$ | 2 | m.p. 119–122° |
| 13 | $C_2H_5$ | $C_2H_5$ | $CH_3$ | $CH_3$ | 2 | |
| 14 | $C_2H_5$ | $C_2H_5$ | $CH_3$ | $C_2H_5$ | 2 | |
| 15 | $CH_3$ | $CH_3$ | $C_3H_{7-i}$ | $CH_3$ | 1 | |
| 16 | $CH_3$ | $CH_3$ | $C_3H_{7-i}$ | $C_3H_{7-i}$ | 2 | m.p. 101–106° |
| 17 | $CH_3$ | $CH_3$ | $C_3H_{7-i}$ | $CH_3$ | 2 | m.p. 113–115,5° |
| 18 | $CH_3$ | $CH_3$ | $CH_3$ | $C_3H_{7-i}$ | 2 | m.p. 129–130° |
| 19 | $CH_3$ | $CH_3$ | $C_2H_5$ | $C_3H_{7-i}$ | 2 | |
| 20 | $CH_3$ | $CH_3$ | $CH_3$ | $C_3H_{7-n}$ | 2 | m.p. 130–131° |
| 21 | $CH_3$ | $CH_3$ | $CH_3$ | $CH_2-CH(CH_3)CH_3$ | 2 | |
| 22 | $CH_3$ | $CH_3$ | $CH_3$ | $C_4H_9-n$ | 2 | m.p. 133–135° |
| 23 | $C_3H_{7-i}$ | $CH_3$ | $CH_3$ | $CH_3$ | 2 | |
| 24 | $C_3H_{7-i}$ | $C_2H_5$ | $CH_3$ | $CH_3$ | 2 | |
| 25 | $CH_3$ | $CH_3$ | $C_3H_{7-i}$ | $C_2H_5$ | 2 | m.p. 124–125,5° |

TABLE II

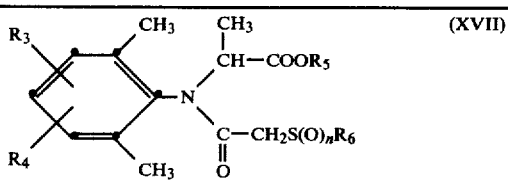

| Comp. No. | R$_3$ | R$_4$ | R$_5$ | R$_6$ | n | |
|---|---|---|---|---|---|---|
| 26 | H | 4-CH$_3$ | CH$_3$ | CH$_3$ | 1 | m.p. 121-124° |
| 27 | H | 4-CH$_3$ | CH$_3$ | CH$_3$ | 2 | |
| 28 | 3-CH$_3$ | 4-CH$_3$ | CH$_3$ | CH$_3$ | 2 | |
| 29 | 3-CH$_3$ | 5-CH$_3$ | CH$_3$ | CH$_3$ | 2 | |
| 30 | H | 5-CH$_3$ | CH$_3$ | CH$_3$ | 2 | |
| 31 | 3-Cl | H | CH$_3$ | CH$_3$ | 2 | |
| 32 | 3-Cl | 5-CH$_3$ | CH$_3$ | CH$_3$ | 2 | |
| 33 | 3-Cl | 5-CH$_3$ | C$_2$H$_5$ | CH$_3$ | 2 | |
| 34 | 3-Cl | 5-CH$_3$ | CH$_3$ | C$_2$H$_5$ | 2 | |
| 35 | 3-C$_3$H$_{7-i}$ | H | CH$_3$ | CH$_3$ | 2 | |
| 36 | 3-C$_3$H$_{7-i}$ | 5-CH$_3$ | CH$_3$ | CH$_3$ | 2 | |
| 37 | 4-Cl | H | CH$_3$ | CH$_3$ | 2 | |

TABLE III

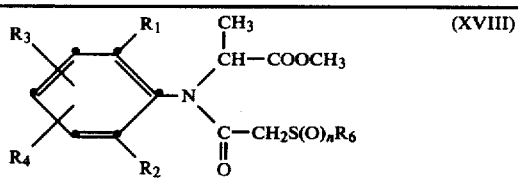

| Comp. No. | R$_1$ | R$_2$ | R$_3$ | R$_4$ | R$_6$ | n |
|---|---|---|---|---|---|---|
| 38 | CH$_3$ | Cl | 3-CH$_3$ | 4-CH$_3$ | CH$_3$ | 2 |
| 39 | CH$_3$ | Cl | H | H | CH$_3$ | 2 |
| 40 | CH$_3$ | Cl | H | 5-CH$_3$ | C$_2$H$_5$ | 2 |
| 41 | Cl | Cl | H | 5-CH$_3$ | CH$_3$ | 2 |
| 42 | Cl | Cl | 3-CH$_3$ | 5-C$_2$H$_5$ | CH$_3$ | 2 |
| 43 | Cl | CH$_3$ | 3-CH$_3$ | 5-CH$_3$ | C$_2$H$_5$ | 2 |
| 44 | Cl | CH$_3$ | 3-Cl | H | CH$_3$ | 2 |
| 45 | Cl | CH$_3$ | 3-Cl | H | CH$_3$ | 1 |
| 46 | Cl | Cl | 3-Cl | H | CH$_3$ | 2 |
| 47 | Cl | CH$_3$ | 3-Cl | 4-CH$_3$ | CH$_3$ | 2 |
| 48 | Cl | CH$_3$ | H | H | C$_3$H$_{7-i}$ | 2 |
| 49 | CH$_3$ | Cl | 3-Cl | 4-CH$_3$ | C$_2$H$_5$ | 2 |
| 50 | CH$_3$ | Cl | H | 4-CH$_3$ | CH$_3$ | 2 |
| 51 | Cl | Cl | 4-Cl | H | CH$_3$ | 1 |
| 52 | OCH$_3$ | CH$_3$ | H | H | CH$_3$ | 1 |
| 53 | OCH$_3$ | CH$_3$ | H | H | CH$_3$ | 2 |
| 54 | OCH$_3$ | OCH$_3$ | H | H | CH$_3$ | 2 |
| 55 | OC$_2$H$_5$ | CH$_3$ | H | H | CH$_3$ | 2 |
| 56 | OC$_2$H$_5$ | OC$_2$H$_5$ | H | H | CH$_3$ | 2 |
| 57 | OC$_3$H$_{7-n}$ | CH$_3$ | H | H | CH$_3$ | 2 |
| 58 | OCH$_3$ | CH$_3$ | 3-CH$_3$ | H | CH$_3$ | 2 |
| 59 | OCH$_3$ | OCH$_3$ | H | H | C$_2$H$_5$ | 2 |
| 60 | OCH$_3$ | OCH$_3$ | H | H | C$_3$H$_{7-i}$ | 2 |
| 61 | OC$_2$H$_5$ | OC$_2$H$_5$ | H | H | C$_3$H$_{7-i}$ | 2 |
| 62 | OCH$_3$ | OCH$_3$ | Cl | H | CH$_3$ | 2 |
| 63 | OCH$_3$ | OCH$_3$ | 3-CH$_3$ | 5-CH$_3$ | CH$_3$ | 2 |

It has been found that compounds having the structure of the formula I surprisingly exhibit a very favourable microbicidal spectrum for practical requirements for the protection of cultivated plants.

The main field of application of compounds of the formula I is in the combating of harmful microorganisms, particularly of phytopathogenic fungi. The compounds of the formula I thus have a very favourable curative and preventive action for protecting cultivated plants without the plants being impaired as a result of undesirable secondary effects. Cultivated plants within the scope of the present invention are for example: cereals (wheat, barley, rye, oats and rice); beet (sugar beet and fodder beet); pomaceous, stone and soft fruit (apples, pears, plums, peaches, almonds, cherries, strawberries, rasberries and blackberries); leguminous plants (beans, lentils, peas and soya bean); oil crops (rape, mustard, poppy, olives, sunflower, coconut, castor-oil plants, cocoa and peanuts); cucurbitaceae (cucumbers, pumpkins and melons); fibre plants (cotton, flax, hemp and jute); citrus fruits (oranges, lemons, grapefruit and mandarins); vegetable varieties (spinach, lettuce, asparagus, cabbage varieties, carrots, onions, tomatoes, potatoes and paprika); or plants such as maize, tobacco, nuts, coffee, sugar cane, grapevines, hops, banana and natural rubber plants, and also ornamental plants.

Microorganisms occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such microorganisms. The active substances are effective against the phytopathogenic fungi belonging to the following classes: Ascomycetes (for example Podosphaera); Basidiomycetes (for example rust fungi, such as Puccinia); Fungi imperfecti (for example Moniliales, such as Cercospora); as well as in particular against the Oomycetes belonging to the Phycomycetes class (for example Phytophthora and Pythium).

Furthermore, the compounds of the formula I have a systemic action. They can moreover be used as dressing agents for the treatment of seed (fruits, tubers, grain, and so forth) and plant cuttings to protect them from fungus infections, and also against microorganisms occurring in the soil.

The present invention thus relates also to the use of the compounds of the formula I for combating and/or preventing an infestation of plants by phytopathogenic microorganisms.

Active substances of the formula I can be used also in admixture with for example pesticidal preparations or with preparations improving plant growth. Active substances of the formula I can be applied simultaneously or successively with other active substances to the areas or the plants to be treated. These active substances can be fertilisers, trace-element agents, or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

The compounds of the formula I can be used on their own or together with suitable carriers and/or other additives. Suitable carriers and additives can be solid or liquid and they correspond to the substances customarily employed in formulation practice, for example natural or regenerated mineral substances, solvents, dispersing agents, wetting agents, adhesives, thickeners, binders or fertilisers. Suitable as dispersing agents, wetting agents and adhesives are the surface-active agents (tensides) common in agricultural chemistry.

By tensides are in this case meant interfacial-active or surface-active compounds which are usually dissolved or dispersed in a liquid, and are preferentally adsorbed at boundary surfaces. A tenside molecule contains at least one group which has an affinity for substances of strong polarity—by which the solubility in water is produced—and at least one further group having negligible affinity for water. Tensides are hence molecules having a lipophil=hydrophobic molecule part, that is to say, a molecule part which is water-repellent or has affinity for fat, usually a hydrocarbon radical having alkyl and/or aryl components, and also a hydrophilic=lipophobic molecule part, that is to say, a molecule part which has affinity for water and is fat-repellent, for example a perfluoroalkyl radical. The products used in practice are in most cases mixtures of compounds of this type. Tensides render possible not only a fine distribution of the active substance in a liquid, for example aqueous, medium but also an increased wettability of the plants: this leads to a reduction in the proportion of active substance in the ready-for-use preparation, and hence to a lower level of contamination of the environment.

The content of active substance in commercial compositions is between 0.01 and 90 percent by weight; the content of additives between 10 and 99.99 percent by weight, the proportion of tenside among the additives being generally 0 to 30 percent by weight.

Compositions of this type are likewise embraced by the present invention.

For application, the compounds of the formula I can be in the following forms (the weight-percentage figures in brackets signify advantageous amounts of active substance):

solid preparations:
  dusts and scattering agents (up to 10%); granulates [coated granules, impregnated granules and homogeneous granules] and pellets (1 to 80%);

Liquid preparations:
  (a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
  (b) solutions (0.1 to 20%); and aerosols.

Production Examples for formulations

EXAMPLE 2

Dusts

The following substances are used to produce (a) a 5% dust, and (b) a 2% dust:

(a)
  5 parts of one of the compounds from the Tables I to III,
  95 parts of talcum;

(b)
  2 parts of one of the compounds from the Tables I to III,
  1 part of highly dispersed silicic acid, and
  97 parts of talcum.

The active substances are mixed and ground with the carriers, and in this form can be applied by dusting.

EXAMPLE 3

Granulate

The following substances are used to produce a 5% granulate:

5 parts of one of the compounds from the Tables I to III,
  0.25 part of epoxidised vegetable oil,
  0.25 part of cetyl polyglycol ether,
  3.50 parts of polyethylene glycol, and
  91 parts of kaolin (particle size 0.3–0.8 mm).

The active substance is mixed with epoxidised vegetable oil, and the mixture is dissolved in 6 parts of acetone, the polyethylene glycol and cetyl polyglycol ether being then added. The solution thus obtained is sprayed onto kaolin, and the acetone is subsequently evaporated in vacuo. A microgranulate of this type is advantageously used for combating soil fungi.

EXAMPLE 4

Wettable powder

The following constituents are used to produce (a) a 70% wettable powder, (b) a 40% wettable powder, (c) and (d) a 25% wettable powder, and (e) a 10% wettable powder:

(a)
  70 parts of one of the compounds from the Tables I to III,
  5 parts of sodium dibutyl-naphthalene sulfonate,
  3 parts of naphthalenesulfonic acid/phenolsulfonic acid/formaldehyde condensate (3:2:1),
  10 parts of kaolin, and
  12 parts of Champagne chalk;

(b)
  40 parts of one of the compounds from the Tables I to III,
  5 parts of sodium lignin sulfonate,
  1 part of sodium dibutyl-naphthalene sulfonate,
  54 parts of silicic acid;

(c)
  25 parts of one of the compounds from the Tables I to III,
  4.5 parts of calcium lignin sulfonate,
  1.9 parts of Champagne chalk/hydroxyethyl cellulose mixture (1:1),
  1.5 parts of sodium dibutyl-naphthalene sulfonate,
  19.5 parts of silicic acid,
  19.5 parts of Champagne chalk, and
  28.1 parts of kaolin;

(d)
  25 parts of one of the compounds from the Tables I to III,
  2.5 parts of isooctylphenoxy-polyoxyethyleneethanol,
  1.7 parts of Champagne chalk/hydroxyethyl cellulose mixture (1:1),
  8.3 parts of sodium aluminium silicate, 16.5 parts of kieselguhr, and
  46 parts of kaolin; and (e)
  10 parts of one of the compounds from the Tables I to III,
  3 parts of a mixture of the sodium salts of saturated fatty alcohol sulfates,
  5 parts of naphthalenesulfonic acid/formaldehyde condensate, and
  82 parts of kaolin.

The active substance is intimately mixed in suitable mixers with the additives, and the mixture is ground in the appropriate mills and rollers. Wettable powders having excellent wetting and suspension properties are obtained. The wettable powders can be diluted with water to obtain suspensions of the required concentration, and these are particularly suitable for leaf application.

EXAMPLE 5

Emulsifiable concentrate

The following substances are used to produce a 25% emulsifiable concentrate:
- 25 parts of one of the compounds from the Tables I to III,
- 2.5 parts of epoxidised vegetable oil,
- 10 parts of an alkylarylsulfonate/fatty alcohol polyglycol ether mixture,
- 5 parts of dimethylformamide, and
- 57.5 parts of xylene.

Emulsions of the required application concentration can be prepared from such concentrates by dilution with water, and they are particularly suitable for leaf application.

The invention embraces also the use of active substances of the formula I for combating and/or preventing an infestation of plants by phytopathogenic microorganisms, the amount of active substance applied per hectare being 50 g to 5 kg, preferably 100 g to 2 kg, and particularly preferably 200 g to 600 g.

Biological Examples

In the following tests Nos 6 and 8, the compound No. 328

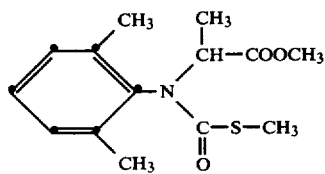

from the German Offenlegungsschrift No. 2,515,091 has been taken as a comparison.

EXAMPLE 6

Action against *Phytophthora infestans* on tomato plants (a) Residual protective action After 3-weeks' cultivation, tomato plants were sprayed with a spray liquor produced from wettable powder of the active substance (0.02% of active substance). After 24 hours, the treated plants were infested with a suspension of sporangia of the fungus. An assessment of the fungus infection was made after incubation of the infested plants during 5 days at 20° with 90-100% relative humidity.

Compared with the fungus infection occurring on the control plants (100% infection), the infection on tomato plants treated with any one of the compounds Nos. 1 to 6, 8, 10, 11, 12, 18, 20 and 26 was reduced to less than 10%. The compounds Nos. 2, 6 and 26 prevented infection completely.

With a proportion of active substance of 0.006%, the comparative substance A resulted in a reduction of infection to 5 to 10%: the compounds Nos. 2, 6 and 26 prevented infection however virtually completely.

(b) Residual curative action

After 3-weeks' cultivation, tomato plants were infested with a suspension of sporangia of the fungus. After an incubation time of 22 hours in a moist chamber at 20° with 90°-100° relative humidity, the infested plants were dried, and then sprayed with a spray liquor prepared from wettable powder of the active substance (0.06% of active substance). After the drying of the applied coating, the treated plants were returned to the moist chamber. An assessment of fungus infection was made 5 days after infestation.

Tomato plants which had been treated with a spray liquor containing one of the compounds of the formula I displayed considerably less fungus infection than that displayed by untreated control plants. In particular the compounds Nos. 1, 2, 3, 6, 18 and 26 reduced infection to 0 to 5%. At a lower test concentration (0.006%), comparative substance A effected indeed a reduction of fungus infection to less than 10%, but the compounds Nos. 1, 2, 3, 6 and 26 still exhibited an unchanged level of activity (0 to 5% infection). Untreated but infested control plants suffered infection to the extent of 100%.

(c) Systemic action

A spray liquor prepared from wettable powder of the active substance (0.006% of active substance, relative to the volume of soil) was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants during 5 days at 20° with 90-100% relative humidity.

The compounds of the formula I exhibited in this test a very good systemic action. Compared with fungus infection occurring on the untreated but infested control plants (100% infection), the infection on tomato plants treated with a spray liquor containing one of the compounds A, 1 to 6, 8, 10, 11, 12, 18 or 26 was only 0 to 5%. Even at a concentration of 0.002%, the compounds Nos. 2, 6, 8, 18 and 26 exhibited undiminished activity.

EXAMPLE 7

Action against *Cercospora arachidicola* on groundnut plants

Residual protective action

Groundnut plants 10-15 cm in height were sprayed with a spray liquor produced from wettable powder of the active substance (0.02% of active substance); and 48 hours later they were infested with a conidiospore suspension of the fungus. The infested plants were incubated for 72 hours at about 21° with high relative humidity, and were subsequently kept in a greenhouse until the typical leaf spots had appeared. The assessment of the fungicidal action was made 12 days after infestation, and was based on the number and size of the occurring spots.

Groundnut plants which had been treated with a spray liquor containing an active substance one of the compounds Nos. 1, 2, 8, 10, 18 and 26 had less than 10% fungus infection, the substance No. 2 preventing infection even completely, whereas the infested but untreated control plants had suffered a 100% level of infection.

EXAMPLE 8

Action against *Pythium debaryanum* on maize plants
Effect after soil application The fungus was cultivated on a carrot-chips nutrient solution, and was then added to a soil/sand mixture. The soil infested in this manner was placed into flower pots, and sown with maize seeds. Immediately after the sowing, the test preparation prepared from wettable powder was poured over the soil (20 ppm of active substance, relative to the soil volume). The pots were then placed for 2-3 weeks in a greenhouse at about 20°. The soil was maintained during this period uniformly moist by light watering.

In the evaluation of the test, the emergence of the maize plants and the proportion of healthy plants and of diseased plants were assessed. The compounds from the Tables I to III exhibited in this test a very good fungicidal action. After treatment with one of the compounds Nos. 1 to 6, 8, 10, 11, 12, 18, 25 or 26, or with the comparative substance A, the maize plants emerged to the extent of over 85% and presented a healthy appearance. In the case of a fourfold dilution, it was still possible to obtain the same effect with the compounds Nos. 2, 6, 8, 18 and 26. Results fully consistent with these results were obtained in analogous tests against Pythium pathogens on sugar beet plants.

EXAMPLE 9

Action against *Podosphaera leucotricha* on apple plants

Residual protective action

Apple seedlings having about 5 developed leaves were sprayed with a spray liquor prepared from wettable powder of the active substance (0.006% of active substance). After 24 hours, the treated plants were infested with a conidiospore suspension of the fungus, and were transferred to a controlled atmosphere chamber at 20° with 70% relative humidity. The assessment of fungus infection was made 12 days after infestation.

The active substances from the Tables I to III exhibited in this test a very good residual-protective action. Apple seedlings which had been treated with one of the compounds Nos. 1, 2, 3, 6, 8, 11, 18 and 26 displayed a degree of fungus infection of less than 20%. The untreated but infested control plants showed 100% infection.

What is claimed is:

1. A compound of the formula I

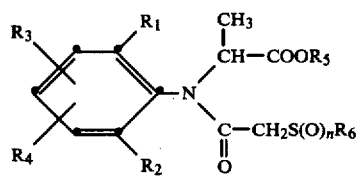

wherein $R_1$ is $C_1$–$C_3$-alkyl, $C_1$–$C_3$-alkoxy or halogen; $R_2$ is $C_1$–$C_3$-alkyl, $C_1$–$C_3$-alkoxy or halogen; $R_3$ is hydrogen, $C_1$–$C_3$-alkyl or halogen; $R_4$ is hydrogen or methyl, $R_5$ is $C_1$–$C_3$-alkyl, $R_6$ is $C_1$–$C_4$-alkyl; and n is 1 or 2.

2. A compound according to claim 1, wherein $R_1$ is $C_1$–$C_2$-alkyl; $R_2$ is $C_1$–$C_2$-alkyl, $C_1$–$C_2$-alkoxy or halogen; $R_3$ is hydrogen, $C_1$–$C_2$-alkyl or halogen; and $R_6$ is $C_1$–$C_3$-alkyl.

3. A compound according to claim 2, wherein $R_1$ is methyl; $R_2$ is methyl, methoxy or chlorine; $R_3$ is hydrogen, methyl or chlorine; $R_5$ is methyl, and n is the number 2.

4. A compound according to claim 2, wherein $R_1$ and $R_2$ are each methyl; $R_3$ is hydrogen, 3-methyl or 3-chlorine; $R_4$ is hydrogen or 5-methyl and $R_5$ is $C_1$–$C_2$-alkyl.

5. The compound N-(1'-methoxycarbonyl-ethyl)-N-methylsulfonylacetyl-2,6-dimethylaniline according to claim 4.

6. The compound N-(1'-methoxycarbonyl-ethyl)-N-ethylsulfonylacetyl-2,6-dimethylaniline according to claim 4.

7. The compound N-(1'-methoxycarbonyl-ethyl)-N-methylsulfonylacetyl-2,3,6-trimethylaniline according to claim 4.

8. A compound of the formula I

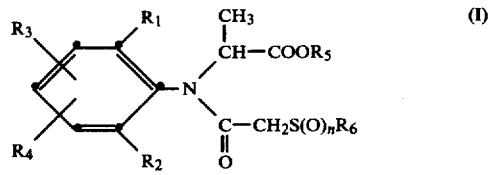

wherein $R_1$ is $C_1$–$C_3$-alkyl, $C_1$–$C_3$-alkoxy or halogen; $R_2$ is $C_1$–$C_3$-alkyl or halogen; $R_3$ is hydrogen, $C_1$–$C_3$-alkyl or halogen; $R_4$ is hydrogen or methyl; $R_5$ is $C_1$–$C_3$-alkyl, $R_6$ is $C_1$–$C_4$-alkyl; and n is 1 or 2.

9. A composition for combating phytopathogenic fungi which comprises a fungicidally effective amount of a compound according to claim 1, and a carrier.

10. A method for combating phytopathogenic fungi which comprises applying to the locus of said fungi a fungicidally effective amount of a compound according to claim 1.

11. A method according to claim 10 in which, in the compound, $R_1$ is $C_1$ or $C_2$ alkyl; $R_2$ is $C_1$ or $C_2$ alkyl, $C_1$ or $C_2$ alkoxy or halogen; $R_3$ is hydrogen, $C_1$ or $C_2$ alkyl or halogen; and $R_6$ is $C_1$–$C_3$ alkyl.

12. A method according to claim 11 in which, in the compound, $R_1$ is methyl; $R_2$ is methyl, methoxy or chlorine; $R_3$ is hydrogen, methyl or chlorine, $R_5$ is methyl; and n is 2.

13. A method according to claim 11 in which, in the compound, $R_1$ and $R_2$ are methyl; $R_3$ is hydrogen, 3-methyl or 3-chlorine; $R_4$ is hydrogen or 5-methyl; and $R_5$ is $C_1$ or $C_2$ alkyl.

14. The method according to claim 13 in which the compound is N-(1'-methoxycarbonyl-ethyl)-N-methylsulfonylacetyl-2,6-dimethylaniline.

15. The method according to claim 13 in which the compound is N-(1'-methoxycarbonyl-ethyl)-N-ethylsuylfonylacetyl-2,6-dimethylaniline.

16. The method according to claim 13 in which the compound is N-(1'-methoxycarbonyl-ethyl)-N-methylsulfonylacetyl-2,3,6-trimethylaniline.

17. A method for combatting phytopathogenic fungi which comprises applying to the locus of said fungi a fungicidally effective amount of a compound according to claim 8.